US008374356B2

(12) United States Patent
Kino et al.

(10) Patent No.: US 8,374,356 B2
(45) Date of Patent: Feb. 12, 2013

(54) NOISE CANCELING APPARATUS AND NOISE CANCELING METHOD

(75) Inventors: Yasuyuki Kino, Tokyo (JP); Yoshio Sasaki, Kanagawa (JP)

(73) Assignee: Sony Corporation, Tokyo (JP)

( * ) Notice: Subject to any disclaimer, the term of this patent is extended or adjusted under 35 U.S.C. 154(b) by 749 days.

(21) Appl. No.: 12/429,714

(22) Filed: Apr. 24, 2009

(65) Prior Publication Data

US 2009/0274320 A1 Nov. 5, 2009

(30) Foreign Application Priority Data

Apr. 30, 2008 (JP) ................................ 2008-118022

(51) Int. Cl.
*A61F 11/06* (2006.01)
*G10K 11/16* (2006.01)
*H03B 29/00* (2006.01)

(52) U.S. Cl. ...................... 381/71.2; 381/71.4; 381/71.8

(58) Field of Classification Search .................... 381/93, 381/95, 96, 86, 71.4, 71.8, 94.1, 122, 71.1, 381/71.3, 111, 58, 59, 71.2
See application file for complete search history.

(56) References Cited

U.S. PATENT DOCUMENTS

2007/0053524 A1 * 3/2007 Haulick et al. .................. 381/92

FOREIGN PATENT DOCUMENTS

JP 02224499 A * 9/1990
JP 3-258099 11/1991
JP 5-344584 12/1993

* cited by examiner

*Primary Examiner* — Phat X Cao
*Assistant Examiner* — Diana C Vieira
(74) *Attorney, Agent, or Firm* — Oblon, Spivak, McClelland, Maier & Neustadt, L.L.P.

(57) ABSTRACT

Disclosed herein is a noise canceling apparatus including: a microphone configured to pick up ambient sound as noise; a first signal generator configured to receive a signal from the microphone to generate a noise cancel signal that is inverted in phase to the signal received from the microphone and has an amplitude level considered with an attenuation in accordance with a distance from the microphone to an observation point separated away from the microphone; a first loudspeaker configured to be arranged in the proximity of the microphone and output the noise cancel signal; a second signal generator configured to receive the signal from the microphone to generate a positive-phase signal that has the same phase as that of the signal from the microphone; and a second loudspeaker configured to be arranged in the proximity of the microphone and output the positive-phase signal.

11 Claims, 11 Drawing Sheets

BACKGROUND ART

NOISE CANCELING APPARATUS AND NOISE CANCELING METHOD

BACKGROUND OF THE INVENTION

1. Field of the Invention

The present invention relates to a noise canceling apparatus and a noise canceling method that are applied to reduce noise inside vehicles for example.

2. Description of the Related Art

Recently, the popularization of portable music reproducing apparatuses has been increasing the occasions of listening music out of doors. For example, listening to music in vehicles, such as trains and buses, the volume of music being reproduced must often be increased to overcome the noise level in such environments. Consequently, the sound leaked from the portable music reproducing apparatus increases, possibly causing trouble to the people around. In order to solve this problem, noise canceling headphones have recently been put in practical use that has noise canceling capabilities of reducing surrounding noise.

For a noise canceling headphone, that based on a feedback scheme is known, for example. In this scheme, a microphone is arranged inside a headphone and the phase of a signal picked up by the microphone as noise (hereafter, this signal will be appropriately referred to as a noise signal) is inverted to generate a signal of inverse phase. This signal having the phase inverse to the phase of noise (hereafter, this signal will be appropriately referred to as a noise cancel signal) is supplied to a driver unit of the headphone, thereby reducing the noise heard by the user.

With the noise canceling headphone based on the feedback scheme, a microphone 101 and a loudspeaker 102 are arranged in the proximity of observation point $P_0$ that is assumed to the position of user ear as shown in FIG. 9, for example. When a noise signal from a noise source is picked up by the microphone 101, a noise cancel signal having a phase that is inverse to the phase of the picked up noise signal is outputted from the loudspeaker 102. At observation point $P_0$, a signal obtained by synthesizing these noise signal and noise cancel signal is observed.

For example, as shown in FIG. 10A, a noise signal with amplitude level "1" is observed at observation point $P_0$. If this noise signal is picked up by the microphone 101, a noise cancel signal with amplitude level "0.9" and phase reverse to the noise signal is outputted from the loudspeaker 102 so as to cancel the noise signal picked up by the microphone 101 as shown in FIG. 10B. It should be noted that, in what follows, the amplitude level and the phase of each noise cancel signal are represented by a number and a sign, respectively. For example, a signal having amplitude level "0.9" and inverted in phase is simply written as "a signal of "−0.9.""

At observation point $P_0$, a noise signal "1" shown in FIG. 10A and a noise cancel signal of "−0.9" shown in FIG. 10B are synthesized and a noise signal attenuated to "0.1" is observed as shown in FIG. 10C. Therefore, the effect of noise cancellation is 1/10 (=−20 dB).

A related-art noise canceling apparatus 100 has a microphone 101, a loudspeaker 102, an analog circuit 103, and an amplifier 104. The microphone 101 converts ambient sound picked up as noise into a noise signal and supplies the noise signal to the analog circuit 103. The analog circuit 103 executes predetermined signal processing on the supplied noise signal to generate a noise cancel signal with phase inverted. The noise cancel signal outputted from the analog circuit 103 is amplified by the amplifier 104 to a predetermined level to be supplied to the loudspeaker 102 to be outputted therefrom.

As described above, the related-art noise canceling method based on the feedback scheme is configured that the effect of noise cancellation is maximized at the position of microphone. Hence, if the microphone and the loudspeaker are arranged in the proximity of the observation point, the effect of noise cancellation can be sufficiently obtained at the observation point.

Also, recently, a method is proposed in which noise canceling capabilities are installed on a car-mounted music reproducing apparatus to reduce noise inside the car. Like the above-mentioned noise canceling headphone, the noise cancellation by the car-mounted music reproducing apparatus is also executed by placing the microphone in the proximity of the loudspeaker mounted on a door of the car. Then, a noise signal detected by the microphone is fed back to the amplifier for driving the loudspeaker and a noise cancel signal inverted in phase to the noise signal is outputted from the loudspeaker, reducing the noise in the proximity of the microphone. For example, Japanese Patent Laid-Open No. Hei 10-333687 describes a noise reducing apparatus for reducing in-car noise.

SUMMARY OF THE INVENTION

In noise cancellation inside a vehicle, such as an automobile, a loudspeaker is often arranged on a door separated away from each seat. This arrangement causes separation between the position of the ears of a user and the position of microphone and the position of loudspeaker. For example, as shown in FIG. 12, suppose that the position of observation point $P_1$ at which the ears of the user are located is separated from the positions of the microphone 101 and the loudspeaker 102. In this example, the distance from observation point $P_1$ to the loudspeaker 102 is 20 cm (centimeters).

Like the above-mentioned example of the noise canceling headphone, when a noise signal from a noise source is picked up by the microphone 101, a noise cancel signal inverted in phase to the noise signal is outputted from the loudspeaker 102. At observation point $P_1$, a signal obtained by synthesizing these noise signal and noise cancel signal is observed.

At observation point $P_1$, a noise signal with amplitude level "1" from a noise source is observed as shown in FIG. 13A, for example. A noise signal from a noise source sufficiently separated away from the observation point can be regarded to be observed with an almost constant acoustic pressure regardless of location, so that a noise signal with amplitude level "1" is picked up also by the microphone 101. If this noise signal is picked up by the microphone 101, a noise cancel signal with "−0.9" is outputted from the loudspeaker 102 so as to cancel the noise signal picked up by the microphone 101.

It is generally known that the acoustic pressure attenuates in proportion to the distance from sound source. In this example, it is assumed that, at a position 20 cm separated away from the loudspeaker 102, the acoustic pressure of a signal outputted from the loudspeaker 102 is approximately 1/4 (=12 dB).

In this case, the noise cancel signal outputted from the loudspeaker 102 attenuates in acoustic pressure by 1/4 until arriving at observation point $P_1$ 20 cm separated away from the loudspeaker 102. Hence, at observation point $P_1$, a noise cancel signal with "−0.225 (=−0.9/4)" is observed as shown in FIG. 13B.

Therefore, at observation point $P_1$, the noise signal with "1" shown in FIG. 13A is synthesized with the noise cancel signal attenuated to "−0.225" shown in FIG. 13B to provide a noise signal with amplitude level "0.775." Namely, the effect of noise cancellation is 0.775 (=−2.2 dB).

As described above, in the related-art noise canceling method based on the feedback scheme, the effect of nose cancellation is maximized at the position of microphone. Hence, if the positions of microphone and loudspeaker are separated away from the observation point, there is a problem that a noise cancel signal outputted from the loudspeaker is attenuated before reaching the observation point, thereby making it unable to provide a sufficient effect of noise cancellation at the observation point.

Therefore, the present invention addresses the above-identified and other problems associated with related-art methods and apparatuses and solves the addressed problems by providing a noise canceling apparatus and a noise canceling method that are configured to execute noise cancellation even at a spot separated away from a microphone and a loudspeaker.

In carrying out the invention and according to one embodiment thereof, there is provided a noise canceling apparatus. This noise canceling apparatus has a microphone configured to pick up ambient sound as noise; a first signal generator configured to receive a signal from the microphone to generate a noise cancel signal that is inverted in phase to the signal received from the microphone and has an amplitude level considered with an attenuation in accordance with a distance from the microphone to an observation point separated away from the microphone; a first loudspeaker configured to be arranged in the proximity of the microphone and output the noise cancel signal; a second signal generator configured to receive the signal from the microphone to generate a positive-phase signal that has the same phase as that of the signal from the microphone; and a second loudspeaker configured to be arranged in the proximity of the microphone and output the positive-phase signal, wherein the noise cancel signal outputted from the first loudspeaker is attenuated by the positive-phase signal outputted from the second loudspeaker to let a noise cancel signal having an amplitude level substantially equal to that of a noise cancel signal observed at the observation point reach the microphone.

In carrying out the invention and according to a second embodiment thereof, there is provided a noise canceling apparatus. This noise canceling apparatus has a microphone configured to pick up ambient sound as noise; a first signal generator configured to receive a signal from the microphone to generate a noise cancel signal that is inverted in phase to the signal received from the microphone and has an amplitude level considered with an attenuation in accordance with a distance from the microphone to an observation point separated away from the microphone; a loudspeaker configured to be arranged in the proximity of the microphone and output the noise cancel signal; a second signal generator configured to receive the noise cancel signal generated by the first signal generator to generate a positive-phase signal inverted in phase to the noise cancel signal; and a synthesizer configured to synthesize the signal from the microphone and the positive-phase signal, wherein the noise cancel signal outputted from the loudspeaker and picked up by the microphone is attenuated by the synthesis with the positive-phase signal in the synthesizer to provide a noise cancel signal having an amplitude level substantially equal to that of a noise cancel signal observed at the observation point.

In carrying out the invention according to a third embodiment thereof, there is provided a noise canceling method. This noise canceling method has the steps of receiving a signal from a microphone picks up ambient sound as noise to generate a noise cancel signal that is inverted in phase to the signal received from the microphone and has an amplitude level considered with an attenuation in accordance with a distance from the microphone to an observation point separated away from the microphone; outputting the noise cancel signal from a first loudspeaker arranged in the proximity of the microphone and; receiving the signal from the microphone to generate a positive-phase signal that has the same phase as that of the signal from the microphone; and outputting the positive-phase signal from a second loudspeaker arranged in the proximity of the microphone, wherein the noise cancel signal outputted from the first loudspeaker is attenuated by the positive-phase signal outputted from the second loudspeaker to let a noise cancel signal having an amplitude level substantially equal to that of a noise cancel signal observed at the observation point reach the microphone.

In carrying out the invention and according to a fourth embodiment thereof, there is provided a noise canceling method. This noise canceling method has the steps of receiving a signal from a microphone that picks up ambient sound as noise to generate a noise cancel signal that is inverted in phase to the signal received from the microphone and has an amplitude level considered with an attenuation in accordance with a distance from the microphone to an observation point separated away from the microphone; outputting the noise cancel signal from a loudspeaker arranged in the proximity of the microphone; receiving the noise cancel signal generated by the first signal generating step to generate a positive-phase signal inverted in phase to the noise cancel signal; and synthesizing the signal from the microphone and the positive-phase signal, wherein the noise cancel signal outputted from the loudspeaker and picked up by the microphone is attenuated by the synthesis with the positive-phase signal in the synthesizing step to provide a noise cancel signal having an amplitude level substantially equal to that of a noise cancel signal observed at the observation point.

As described above, in the first and third embodiments of the invention, a signal from a microphone for picking up ambient sound as noise is supplied, a noise cancel signal inverted in phase to the supplied signal and having amplitude level considered with an attenuation in accordance with a distance from the microphone to an observation point separated away from the microphone is generated, the noise cancel signal is outputted from a first loudspeaker arranged in the proximity of the microphone, the signal from the microphone is supplied to generate a positive-phase signal having the same phase as that of the signal from the microphone, the positive-phase signal is outputted from a second loudspeaker arranged in the proximity of the microphone, the noise cancel signal outputted from the first loudspeaker is attenuated by the positive-phase signal outputted from the second loudspeaker, and a noise cancel signal having an amplitude level substantially equal to that of the noise cancel signal observed at the observation point reaches the microphone. This configuration allows the creation of a virtual state where the microphone were arranged in the proximity of the observation point.

In the second and fourth embodiments of the invention, a signal from a microphone for picking up ambient sound as noise is supplied, a noise cancel signal inverted in phase to the supplied signal and having an amplitude level considered with an attenuation in accordance with a distance from the microphone to an observation point separated away from the microphone is generated, the noise cancel signal is outputted from a loudspeaker arranged in the proximity of the microphone, the noise cancel signal generated by the first signal generating step is supplied to generate a positive-phase signal inverted in phase to the noise cancel signal, the signal from the microphone and the positive-phase signal are synthesized, the noise cancel signal outputted from the loudspeaker and picked up by the microphone is attenuated by the synthesis with the positive-phase signal in the synthesizing step, and a noise cancel signal having an amplitude level substantially equal to that of the noise cancel signal observed at the observation point is provided. This configuration allows the creation of a virtual state where the microphone were arranged in the proximity of the observation point.

The embodiments of the present invention are configured such that a noise cancel signal outputted from a loudspeaker to be picked up by a microphone is attenuated by a positive-phase signal to let the noise cancel signal having an amplitude level substantially equal to that of the noise cancel signal to be observed at an observation point reach the microphone. Consequently, the embodiments of the present invention provides effects that, even if the microphone is arranged at a spot separated away from the observation point, a virtual state in which the microphone were arranged in the proximity of the observation point can be created, thereby allowing noise cancellation at the observation point separated away from the microphone.

BRIEF DESCRIPTION OF THE DRAWINGS

The above and other features and advantages of the invention will become apparent from the following description of embodiments with reference to the accompanying drawings in which.

DETAILED DESCRIPTION OF THE PREFERRED EMBODIMENTS

This invention will be described in further detail by way of embodiments thereof with reference to the accompanying drawings. In one embodiment of the present invention, a microphone and a loudspeaker are arranged at spots separated away from an observation point and noise cancellation can be executed at a spot separated away from the loudspeaker.

Figure 1:
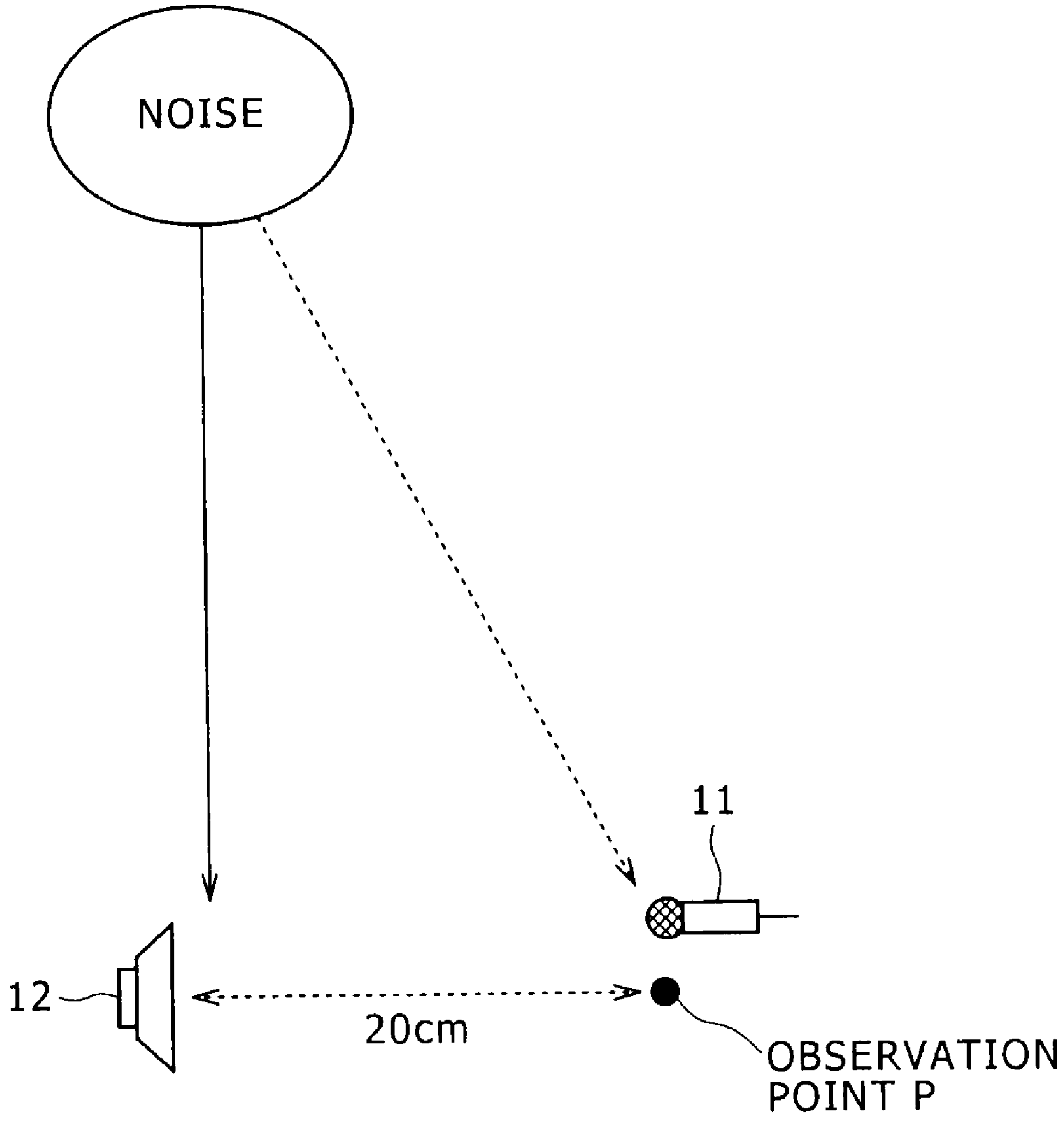
FIG. 1 is a schematic diagram illustrating a noise canceling method in the case where a microphone is arranged in the proximity of an observation point located a spot separated away from a loudspeaker.

First, in order to facilitate the understanding of one embodiment of the invention, a noise canceling method in which a microphone is arranged in the proximity of an observation point located at a spot separated away from a loudspeaker will be described. For example, as shown in FIG. 1, a microphone 11 is arranged in the proximity of observation point P 20 cm separated away from a spot where a loudspeaker 12 is arranged.

When a noise signal from the sound source is picked by the microphone 11, a noise cancel signal inverted in phase to the noise signal is outputted from the loudspeaker 12. At observation point P, a signal obtained by synthesizing these noise signal and noise cancel signal is observed.

It should be noted that, in the noise canceling method based on the feedback scheme, the effect of noise cancellation is maximized at the position of microphone. Therefore, a noise cancel signal is outputted from the loudspeaker 12 such that the effect of noise cancellation is made maximum at the position of the microphone 11. For example, if it is assumed that the acoustic pressure be attenuated to ¼ (−20 dB) at a spot 20 cm separated away from the loudspeaker 12, a noise cancel signal having an amplitude level four times as high is outputted from the loudspeaker 12 by taking an attenuation according to the distance to the microphone 11 into consideration.

Figure 2A:
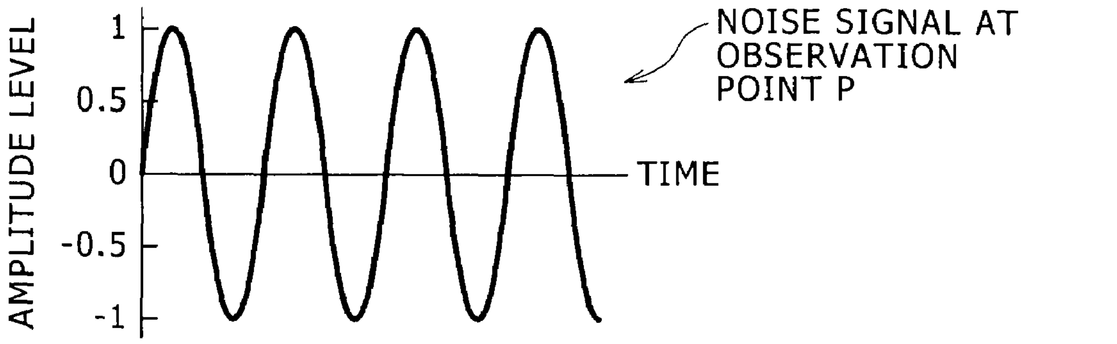
FIGS. 2A, 2B, 2C, and 2D are diagrams illustrating waveforms of signals provided in the case where a microphone is arranged in the proximity of an observation point located at a spot separated away from a loudspeaker.
Figure 2B:
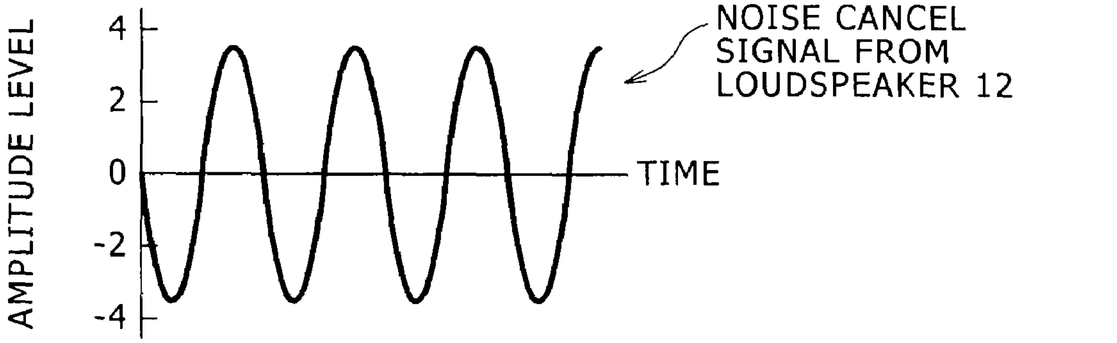

At observation point P, as shown in FIG. 2A for example, a noise signal with amplitude level “1” from the noise source is observed to be picked up by the microphone 11. If this noise signal is picked up by the microphone 11, the loudspeaker 12 outputs a noise cancel signal with amplitude level “3.6” and inverted in phase to the noise signal so as to cancel the noise signal picked up by the microphone 11 as shown in FIG. 2B by considering an attenuation according to the distance between the microphone 11 and the loudspeaker 12. It should be noted that, in what follows, the amplitude level and the phase of each noise cancel signal are represented by number and sign. For example, “a signal having an amplitude level of “3.6” and inverted in phase to a noise signal” is simply expressed as “a signal “−3.6.””

Figure 2C:
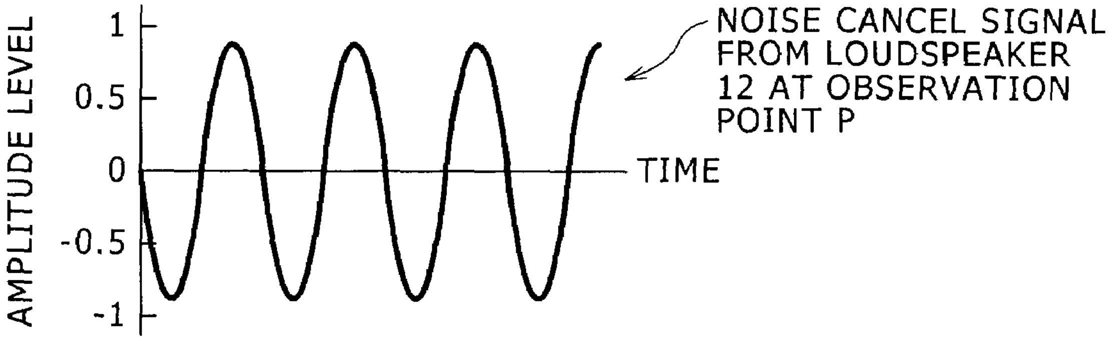
Figure 2D:
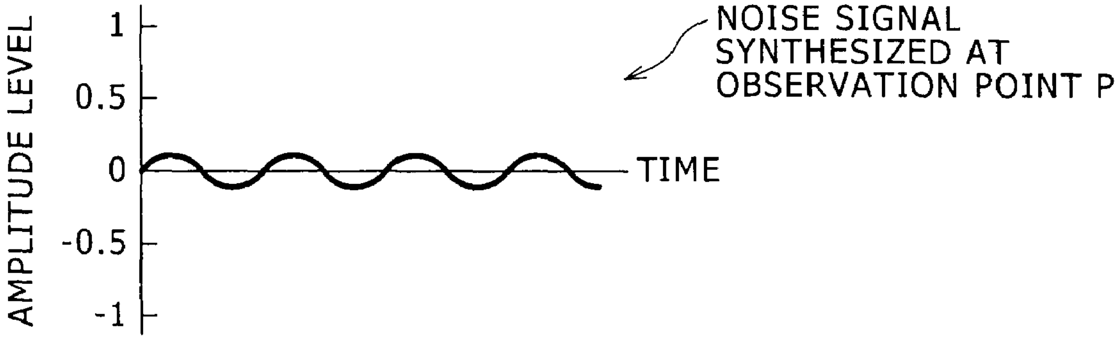

At observation point P, as shown in FIG. 2C, a noise cancel signal “−0.9” obtained by attenuating a noise cancel signal “−3.6” by ¼ outputted from the loudspeaker 12 is observed. Then, the noise signal “1” shown in FIG. 2A is synthesized with the noise cancel signal “−0.9” shown in FIG. 2C to provide a noise signal with amplitude level attenuated to “0.1” that is observed as shown in FIG. 2D.

Thus, arranging the microphone 11 in the proximity of observation point P located at a spot separated away from the loudspeaker 12 allows the noise cancellation in which the effect of noise cancellation is maximized at observation point P.

Actually, however, because observation point P is at the position of the ear of user, it is difficult to arrange the microphone 11 in the proximity of observation point P. Therefore, in this embodiment of the invention, a configuration is provided in which, if a microphone is arranged in the proximity of a loudspeaker arranged at a spot separated away from an observation point, a virtual state is created as if the microphone be arranged in the proximity of the observation point. Further, noise is reduced at the position of observation point that is separated away from the loudspeaker.

Figure 3:
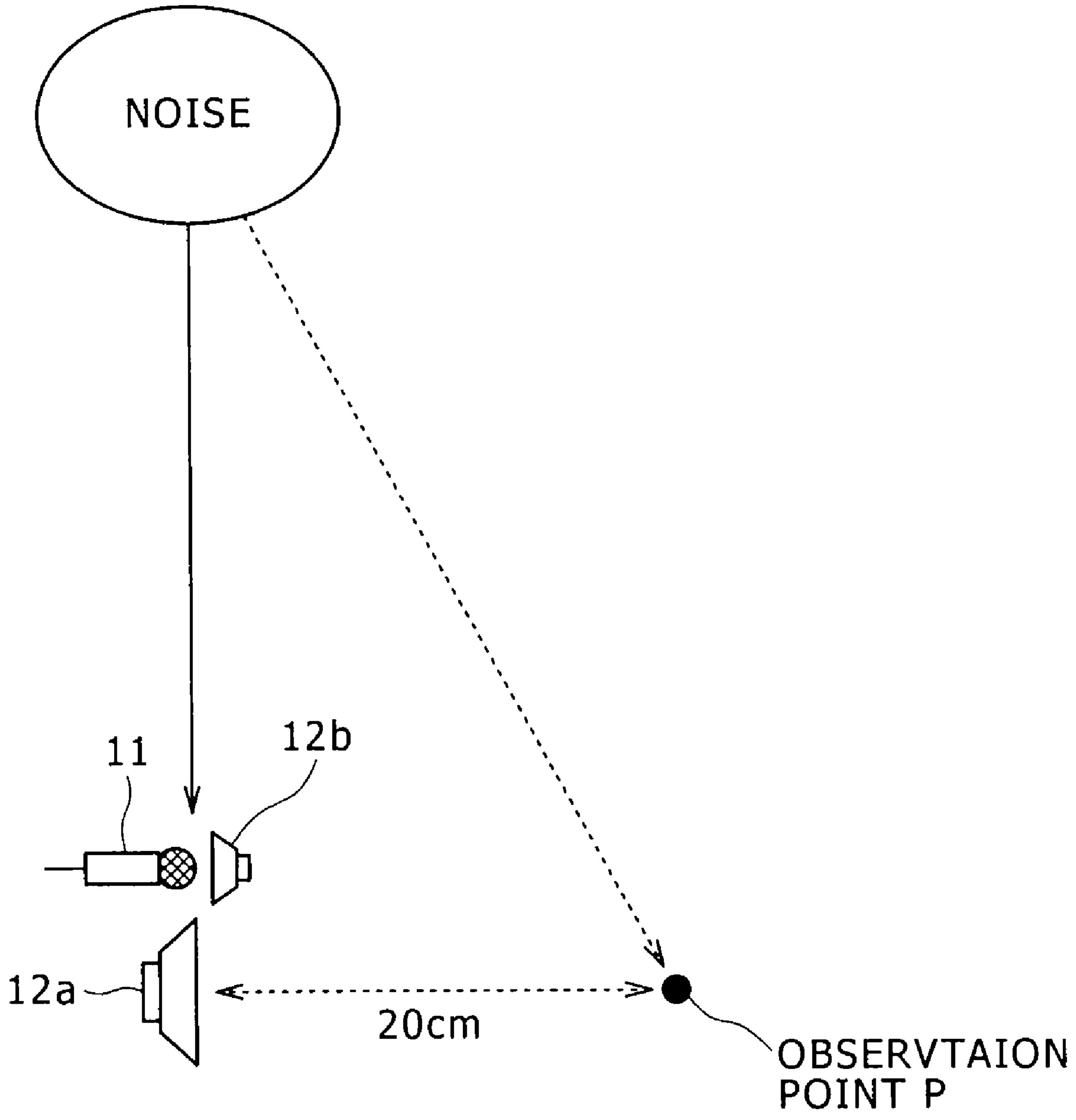
FIG. 3 is a schematic diagram illustrating for describing a noise canceling method practicable as one embodiment of the present invention.

In one embodiment of the invention, the microphone 11 and a main loudspeaker 12*a* are arranged close to each other at spots separated away from observation point P that is the position of the ear of user and a sub loudspeaker 12*b* is additionally arranged as shown in FIG. 3, for example. Namely, an example is shown here in which the microphone 11, the main loudspeaker 12*a*, and the sub loudspeaker 12*b* are arranged at spots approximately 20 cm separated away from observation point P.

The microphone 11 is arranged such that the signals outputted from the main loudspeaker 12*a* and the sub loudspeaker 12*b* are entered in the microphone 11. The sub loudspeaker 12*b* is arranged such that the distance to the microphone 11 is shorter than the distance from the main loudspeaker 12*a* to the microphone 11. Also, the sub loudspeaker 12*b* is arranged in an orientation in which it is difficult for a signal outputted from the sub loudspeaker 12*b* is difficult to observe at observation point P.

The main loudspeaker 12*a* outputs a noise cancel signal inverted in phase to the noise signal from the noise source. The sub loudspeaker 12*b* outputs a signal inverted in phase to the noise cancel signal outputted from the main loudspeaker 12*a*, namely, a positive-phase signal having the same phase as the noise signal. The microphone 11 picks up a signal obtained by synthesizing the noise cancel signal outputted from the main loudspeaker 12*a* and the signal outputted from the sub loudspeaker 12*b*.

The following describes a noise canceling method in which at observation point P when the microphone 11, the main loudspeaker 12*a*, and the sub loudspeaker 12*b* are arranged relative to observation point P as shown in FIG. 3. In the example shown in FIG. 3, normal noise canceling causes the main loudspeaker 12*a* to output a noise cancel signal inverted in phase to a noise signal. Also, a positive-phase signal having a relatively low acoustic pressure than the noise cancel signal is outputted from the sub loudspeaker 12*b*. The microphone 11 picks up a signal obtained by synthesizing the noise cancel signal outputted from the main loudspeaker 12*a* and the positive-phase signal outputted from the sub loudspeaker 12*b*.

At this moment, the distance from the sub loudspeaker 12*b* to the microphone 11 is shorter than the distance from the main loudspeaker 12*a* to the microphone 11. Hence, if a positive-phase signal is outputted from the sub loudspeaker 12*b* with a relatively low acoustic pressure, the acoustic pressure of the positive-phase signal outputted from the sub loudspeaker 12*b* observed at the position of the microphone 11 is almost equal to the acoustic pressure of the noise cancel signal outputted from the main loudspeaker 12*a*.

Therefore, at the position of the microphone 11, the noise cancel signal from the main loudspeaker 12*a* and the positive-phase signal from the sub loudspeaker 12*b* cancel each other to put an inverted-phase signal having a very low acoustic pressure into the microphone 11.

Thus, the acoustic pressure of a signal to be entered in the microphone 11 is lowered by canceling the noise cancel signal inverted in phase to the noise signal by the positive-phase signal. This configuration enables the virtual creation of the same state as a state in which the microphone 11 is arranged in the proximity of observation point P located at a spot separated away from the loudspeaker 12 as shown in FIG. 1 regardless of the arrangement of the microphone 11 separated away from observation point P.

Figure 4A:
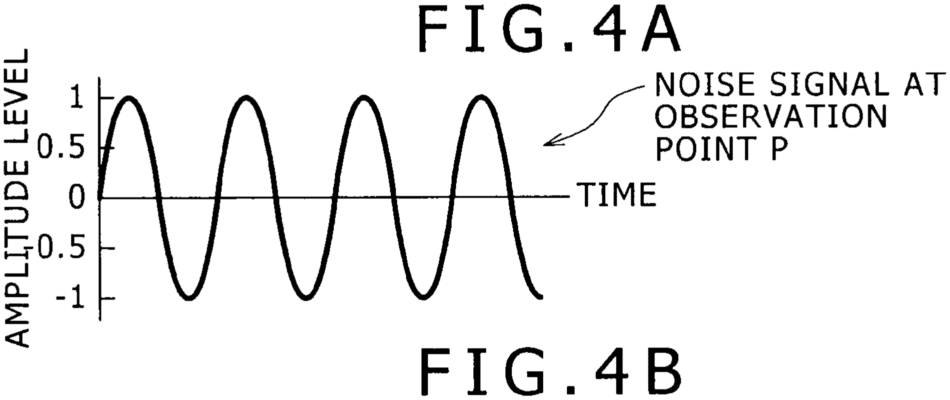
FIGS. 4A, 4B, 4C, 4D, and 4E are diagrams illustrating waveforms of signals in the case where the noise canceling method shown in FIG. 3 is used.

For example, at observation point P, a noise signal with amplitude level "1" from the noise source is observed as shown in FIG. 4A. In addition, as described above in "Background of The Invention" herein, a noise signal from a sufficiently separated noise source can be regarded as observable at an approximately constant acoustic pressure independently of location, so that a noise signal with amplitude level "1" is observed in the same manner also at the spot where the microphone 11 is arranged.

From the main loudspeaker 12*a*, a noise cancel signal is outputted to cancel the noise signal. At this moment, in the present embodiment, the effect of noise cancellation is maximized at observation point P. To do so, a noise cancel signal with "−0.9" for canceling the noise signal "1" must be observed at observation point P. So, the main loudspeaker 12*a* outputs a noise cancel signal with an attenuation according to the distance from the microphone 11 and the main loudspeaker 12*a* to observation point P considered.

Figure 4B:
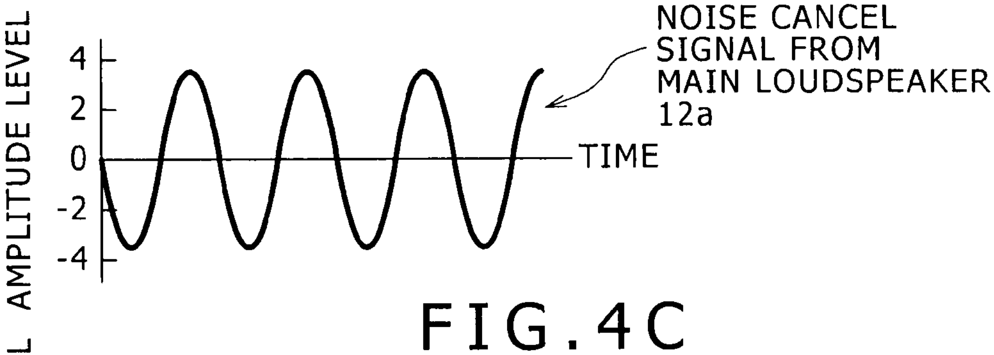

In this example, it is assumed that the distance from the microphone 11 and the main loudspeaker 12*a* to observation point P be 20 cm and the acoustic pressure be attenuated to ¼ (−20 dB) at a spot 20 cm separated away from the main loudspeaker 12*a*. In this case, the main loudspeaker 12*a* outputs a noise cancel signal of "−3.6" that is an amplitude level four times as high as shown in FIG. 4B.

Figure 4C:
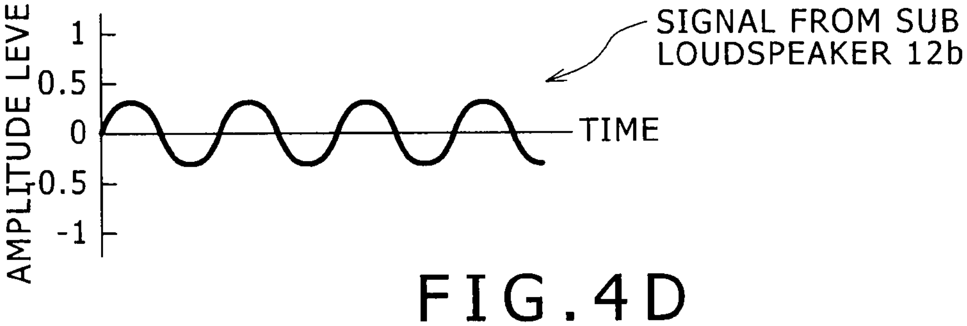

On the other hand, the sub loudspeaker 12*b* outputs a positive-phase signal for canceling a noise cancel signal outputted from the main loudspeaker 12*a* so as to make a noise cancel signal to be entered in the microphone 11 have the same amplitude level as that of noise cancel signal observed at observation point P. At this moment, the positive-phase signal outputted from the sub loudspeaker 12*b* is outputted after amplification thereof has been adjusted so as to set the amplitude level to a desired level. In this example, the amplitude is adjusted to set the amplitude level of the positive-phase signal to "0.3" as shown in FIG. 4C, for example.

Therefore, the microphone 11 picks up a signal obtained by synthesizing the noise cancel signal "−3.6" outputted from the main loudspeaker 12*a*, the positive-phase signal "0.3" outputted from the sub loudspeaker 12*b*, and the noise signal "1" from the noise source.

Figure 4D:
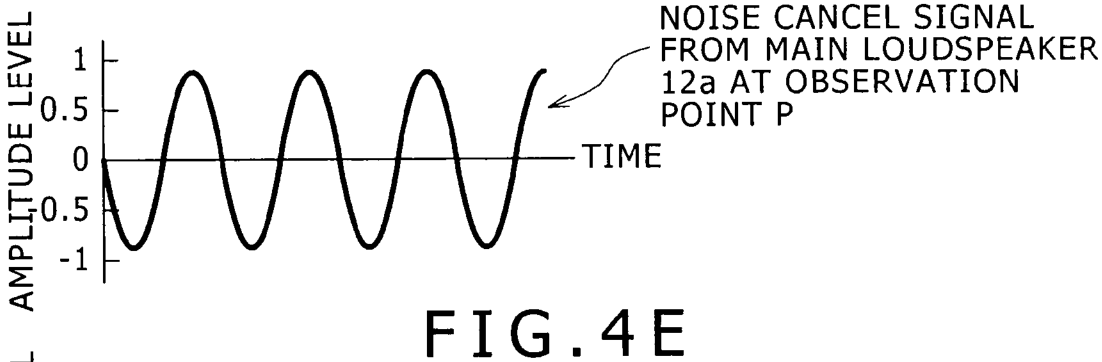
Figure 4E:
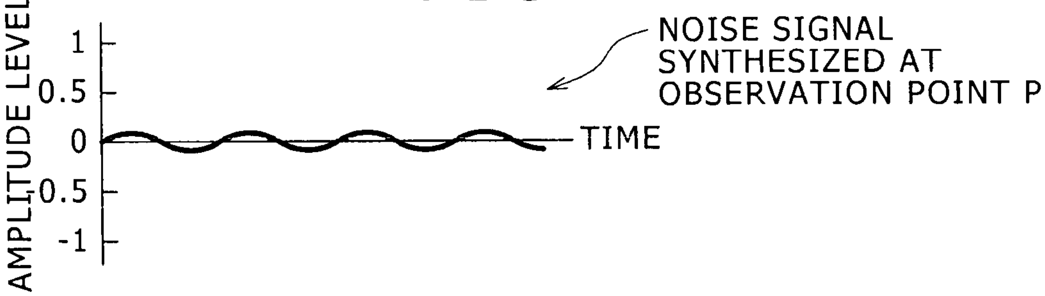

At observation point P, a noise cancel signal "−0.9" obtained by attenuating a noise cancel signal "−3.6" outputted from the main loudspeaker 12*a* to ¼ is observed as shown in FIG. 4D. Then, the noise signal "1" from the noise source shown in FIG. 4A and the noise cancel signal "−0.9" shown in FIG. 4D are synthesized and a noise signal with amplitude level attenuated to "0.1" is observed as shown in FIG. 4E.

Thus, in the present embodiment of the invention, the noise cancel signal component to be entered in the microphone 11 is adjusted to be equivalent to the noise cancel signal at observation point P by use of the sub loudspeaker 12*b*. This adjustment allows the execution of noise canceling such that the effect of noise cancellation is maximized at observation point P separated away from the spot at which the main loudspeaker 12*a* is arranged, in the same manner as the arrangement of the microphone 11 in the proximity of observation point P.

It should be noted that, in the present embodiment of the invention, the amplitude level of a positive-phase signal outputted from the sub loudspeaker 12*b* can be adjusted in accordance with the distance from the microphone 11 and the main loudspeaker 12*a* to observation point P to maximize the effect of noise cancellation at a desired spot.

For example, increasing the amplitude level of a positive-phase signal to be outputted from the sub loudspeaker 12*b* reduces the amplitude level of a noise cancel signal to be entered in the microphone 11 obtained by synthesizing this positive-phase signal and the noise cancel signal outputted from the main loudspeaker 12*a*. Hence, the effect of noise cancellation can be maximized at a spot separated away from the main loudspeaker 12*a*.

Also, lowering the amplitude level of a positive-phase signal to be outputted from the sub loudspeaker 12*b* increases the amplitude level of a noise cancel signal to be entered in the microphone 11. So, the effect of noise cancellation can be maximized at a spot nearer to the main loudspeaker 12*a*.

Figure 5:
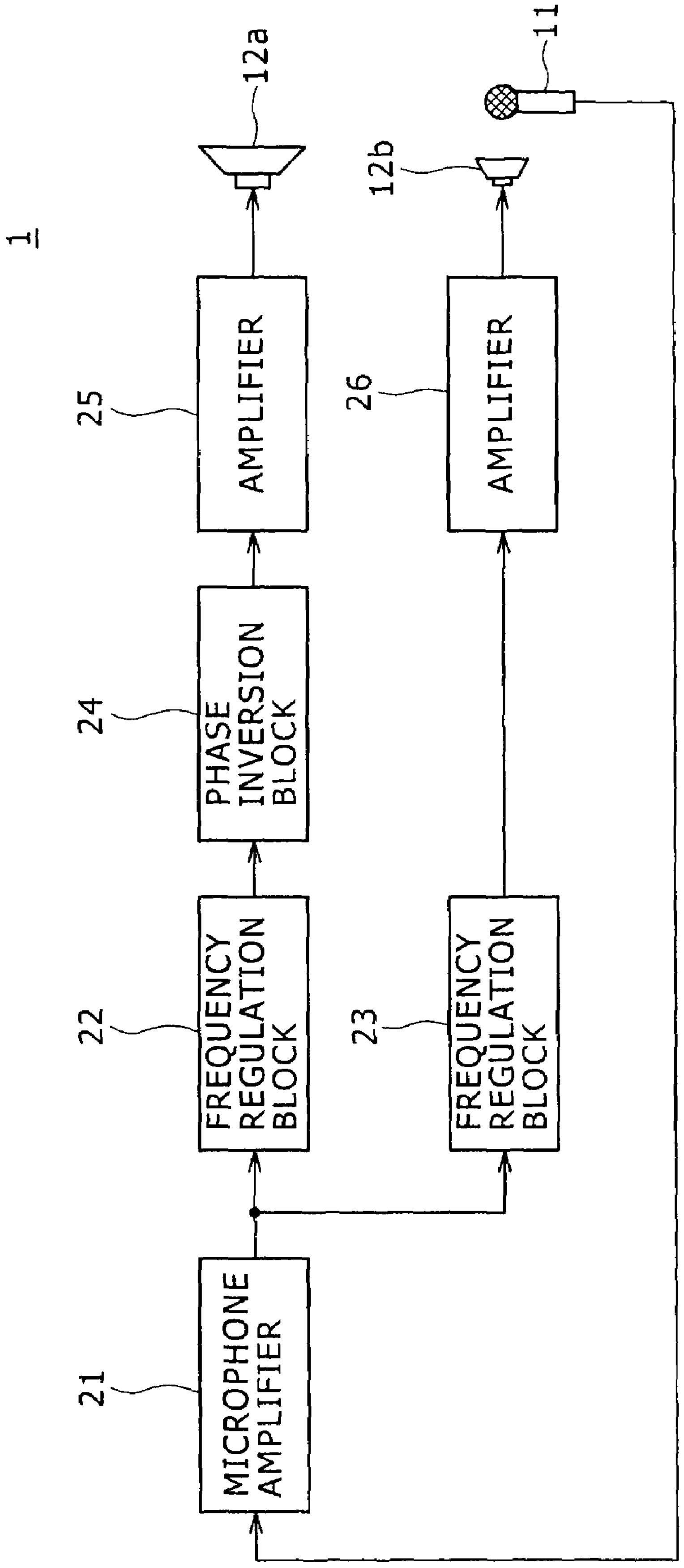
FIG. 5 is a block diagram illustrating an exemplary configuration of a noise canceling apparatus practiced as one embodiment of the present invention.

The following describes one configuration of a noise canceling apparatus 1 that can be practiced as one embodiment of the invention with reference to FIG. 5. The noise canceling apparatus 1 has a microphone amplifier 21, a frequency regulation blocks 22 and 23, a phase inversion block 24, and amplifiers 25 and 26, to which a microphone 11, a main loudspeaker 12*a*, and a sub loudspeaker 12*b* are connected. The microphone 11 converts an ambient sound picked up as noise into a noise signal, which is supplied to the microphone amplifier 21. The microphone amplifier 21 amplifies the supplied noise signal to a predetermined level and supplies the amplified noise signal to the frequency regulation blocks 22 and 23.

The frequency regulation block 22, which is an LPF (Low Pass Filter) or an equalizer, for example, blocks frequency components other than of the low area of the frequency components of the supplied noise signal and changes the frequency characteristics of the noise signal, for example. The phase inversion block 24 inverts the phase of the supplied noise signal to generate a noise cancel signal inverted in phase to the noise signal. The noise cancel signal outputted from the phase inversion block 24 is supplied to the main loudspeaker 12*a* through the amplifier 25 to be outputted from the main loudspeaker 12*a*.

The frequency regulation block 23 regulates the frequency characteristics of the supplied signal in a predetermined manner. The signal outputted from the frequency regulation block 23 is supplied to the sub loudspeaker 12*b* through the amplifier 26 to be outputted from the sub loudspeaker 12*b*. The amplification by the amplifier 26 is variable, which can be varied in accordance with the distance from the microphone 11 and the main loudspeaker 12*a* to observation point P.

For example, a signal to be outputted from the sub loudspeaker 12*b* is outputted with a lower acoustic pressure than the acoustic pressure of a noise cancel signal to be outputted from the main loudspeaker 12*a*, so that the sub loudspeaker 12*b* may be smaller in diaphragm diameter than the main loudspeaker 12*a*.

However, generally, loudspeakers are different in frequency characteristic depending on the diameter of diaphragm. Especially, with loudspeakers having relatively smaller diaphragm diameters, the frequency characteristic on the low side of a signal deteriorates. Hence, if a loudspeaker having a diaphragm diameter smaller than that of the main loudspeaker 12*a* is used for the sub loudspeaker 12*b*, the frequency component of the low side has to be amplified by the frequency regulation block 23 to regulate the frequency characteristic of each noise signal. Thus, regulating the frequency characteristic of the low side of each noise signal can provide the substantially the same frequency characteristic as that of a loudspeaker having a relatively large diaphragm diameter used as the main loudspeaker 12*a*.

Figure 6:
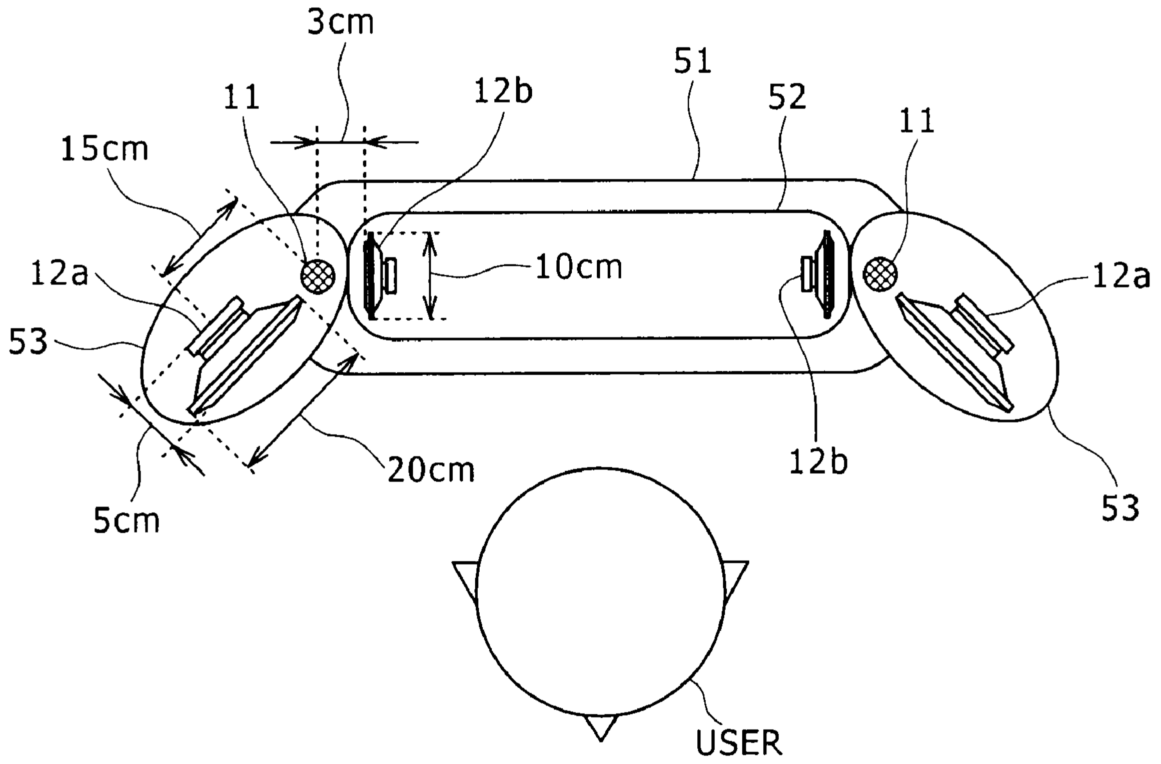
FIG. 6 is a schematic diagram illustrating an installation example provided when the noise canceling apparatus shown in FIG. 5 is applied to an automobile.

FIG. 6 shows an installation example in which the noise canceling apparatus 1 according to one embodiment of the invention is applied to an automobile. On the upper part of a back rest 51, a head rest 52 is amounted with a support bar or the like. On the left and right sides of the head rest 52, loudspeaker units 53 for the right channel and left channel are mounted.

In each loudspeaker unit 53, the microphone 11 and the loudspeaker 12 are arranged in the proximity of each other. The loudspeaker unit 53 is mounted on the head rest 52 for example.

On each side inside the head rest 52, the sub loudspeaker 12*b* is arranged. The loudspeaker 12 is arranged such that the sub loudspeaker 12*b* is oriented in the direction of the microphone 11 so that an outputted signal is surely picked up by the microphone 11, thereby making it hard for the signal outputted from the sub loudspeaker 12*b* to be observed at the potion of the user ears.

It should be noted that the mounting position of the loudspeaker unit 53 is not restricted to the position shown in this example; for example, the loudspeaker unit 53 may be mounted on the back rest 51. Also, a configuration may be practicable in which the loudspeaker unit 53 is unitized with the head rest 52, for example.

As described above, in the present embodiment of the invention, the acoustic pressure of a signal outputted from the sub loudspeaker 12*b* is lower than the acoustic pressure of a signal outputted from the main loudspeaker 12*a*. Therefore, the diaphragm diameter of a loudspeaker used for the sub loudspeaker 12*b* may be smaller than that of a loudspeaker used for the main loudspeaker 12*a*. In this example, for the main loudspeaker 12*a*, a loudspeaker having a diaphragm diameter of 20 cm and a thickness of 5 cm may be used. For the sub loudspeaker 12*b*, a loudspeaker having a diaphragm diameter of 10 cm may be used.

Further, the sub loudspeaker 12*b* is arranged at a spot that is nearer than the distance from the microphone 11 to the main loudspeaker 12*a*. In this example, the distance from the center of the main loudspeaker 12*a* to the microphone 11 is set to 15 cm for example and the distance from the sub loudspeaker 12*b* to the microphone 11 is set to 3 cm for example.

Next, the following describes a first variation to the above-mentioned embodiment of the invention. In the first variation to the above-mentioned embodiment, a microphone and a loudspeaker are arranged in the proximity of each other at spots separated away from an observation point. And, inside a noise canceling apparatus, a noise cancel signal component to be picked up by the microphone is attenuated at a stage immediately after the input in the microphone, thereby providing a virtual state in which the microphone is arranged as if in the proximity of the observation point.

Figure 7:
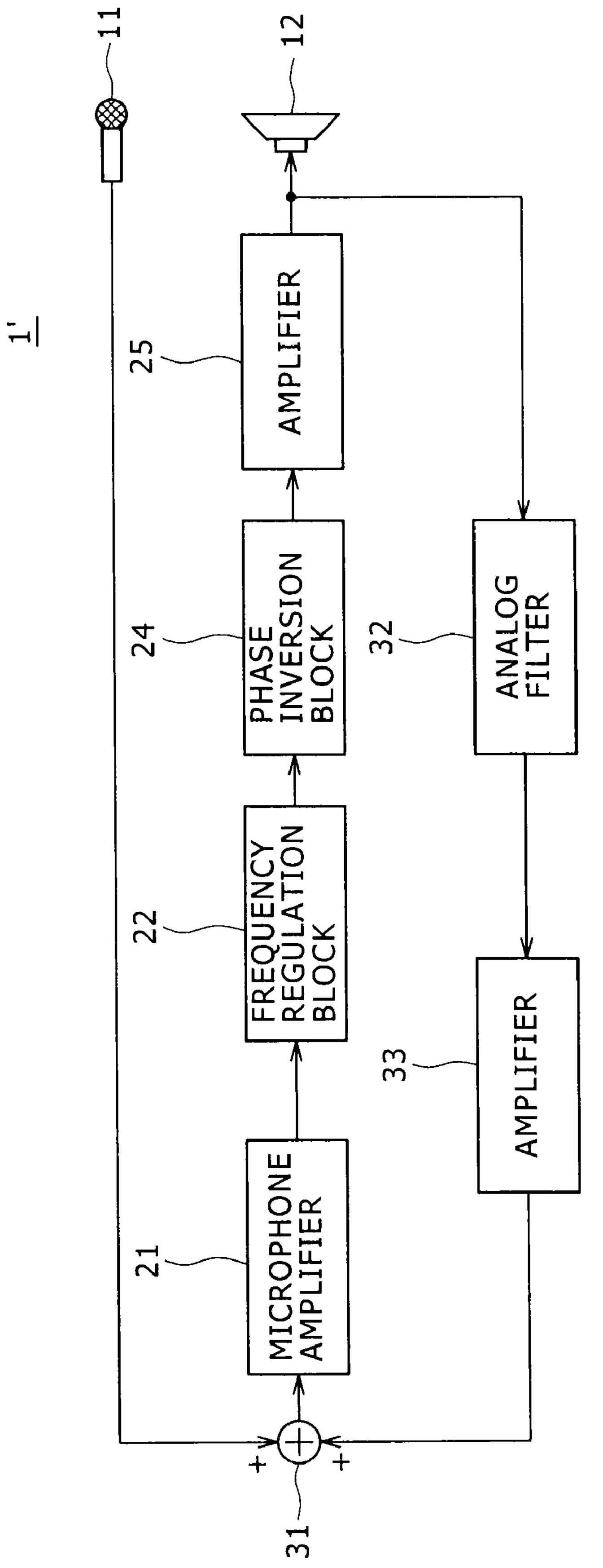
FIG. 7 is a block diagram illustrating an exemplary configuration of a noise canceling apparatus practiced as a first variation to the above-mentioned embodiments.

The following describes an exemplary configuration of a noise canceling apparatus 1' that is applicable to the first variation of the above mentioned embodiment of the invention with reference to FIG. 7. The noise canceling apparatus 1' has a microphone amplifier 21, a frequency regulation block 22, a phase inversion block 24, an amplifier 25, an adder 31, an analog filter 32, and an amplifier 33 and is connected with a microphone 11 and a loudspeaker 12. It should be noted that, with reference to FIG. 7, components similar to those of the above-mentioned embodiment are denoted by the same reference numerals and the description thereof will be skipped.

A noise signal picked up by the microphone 11 is supplied to the adder 31. The adder 31 adds the noise signal entered from the microphone 11 to a signal outputted from the amplifier 33. A signal outputted from the adder 31 is amplified by the microphone amplifier 21 to a predetermined level. The frequency component of the amplified signal is regulated by the frequency regulation block 22 in a predetermined manner. Then, a noise cancel signal inverted in phase is generated by the phase inversion block 24 to be outputted from the loudspeaker 12 via the amplifier 25.

Also, the generated noise cancel signal is supplied to the analog filter 32. The analog filter 32 executes the processing of regulating the frequency characteristic of the supplied signal in a predetermined manner and, at the same time, inverts the phase of the signal to generate a positive-phase signal inverted in phase to the noise cancel signal, namely, having the same phase as that of the noise signal. This positive-phase signal is a signal that has substantially equal amplitude level and phase characteristic to those of the positive-phase signal outputted from the sub loudspeaker 12*b* in the noise canceling apparatus 1.

The amplifier 33 amplifies the signal supplied from the analog filter 32 to a predetermined level. The amplification by the amplifier 33 is variable and can be varied in accordance with the distance from the microphone 11 and the loudspeaker 12 to observation point P. For example, if the distance from the microphone 11 and the loudspeaker 12 to observation point P is relatively far, the amplification by the amplifier 33 is increased. If the distance from the microphone 11 and the loudspeaker 12 to observation point P is relatively near, the amplification by the amplifier 33 is decreased.

Thus, attenuating the noise cancel signal component to be entered in the microphone 11 immediately after the noise cancel signal has been entered in the microphone 11 makes the noise cancel signal component at the succeeding stage of the microphone 11 be put in the substantially the same signal as the noise cancel signal that is observed at observation point P. Namely, the microphone 11 is put in substantially the same state as arranged in the proximity of observation point P, thereby maximizing the effect of noise cancellation at observation point P.

The following describes a second variation to the above-mentioned embodiment of the invention. The noise canceling apparatuses according to the above-mentioned embodiment and the first variation thereto are configured to maximize the effect of noise cancellation at an observation point separated away from a microphone and a loudspeaker. However, if these noise canceling apparatuses are applied to automobiles and the like for example, it is considered that the position of the head of a seated user is not always in a fixed state but is moving in accordance with ambient situations. Hence, if the position of user that is an observation point gets out of a predetermined spot, the distance from the microphone and the loudspeaker changes, thereby making it difficult to provide a sufficient effect of noise cancellation.

Therefore, the second variation to the above-mentioned embodiment is configured such that the distance from the microphone and the loudspeaker to the observation point is measured and, even if there occurs a change of the position of the observation point depending on the measured distance, the effect of noise cancellation is maximized.

Figure 8:
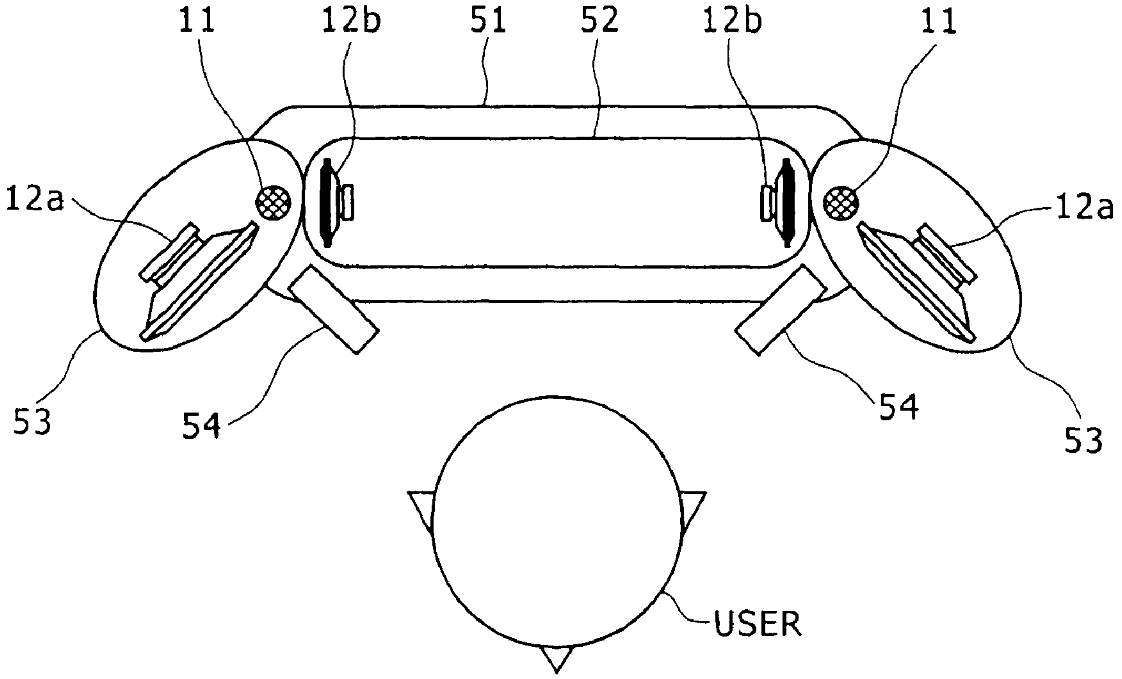
FIG. 8 is a schematic diagram illustrating an installation example provided when a noise canceling apparatus practiced as a second variation to the above-mentioned embodiments.
Figure 9:
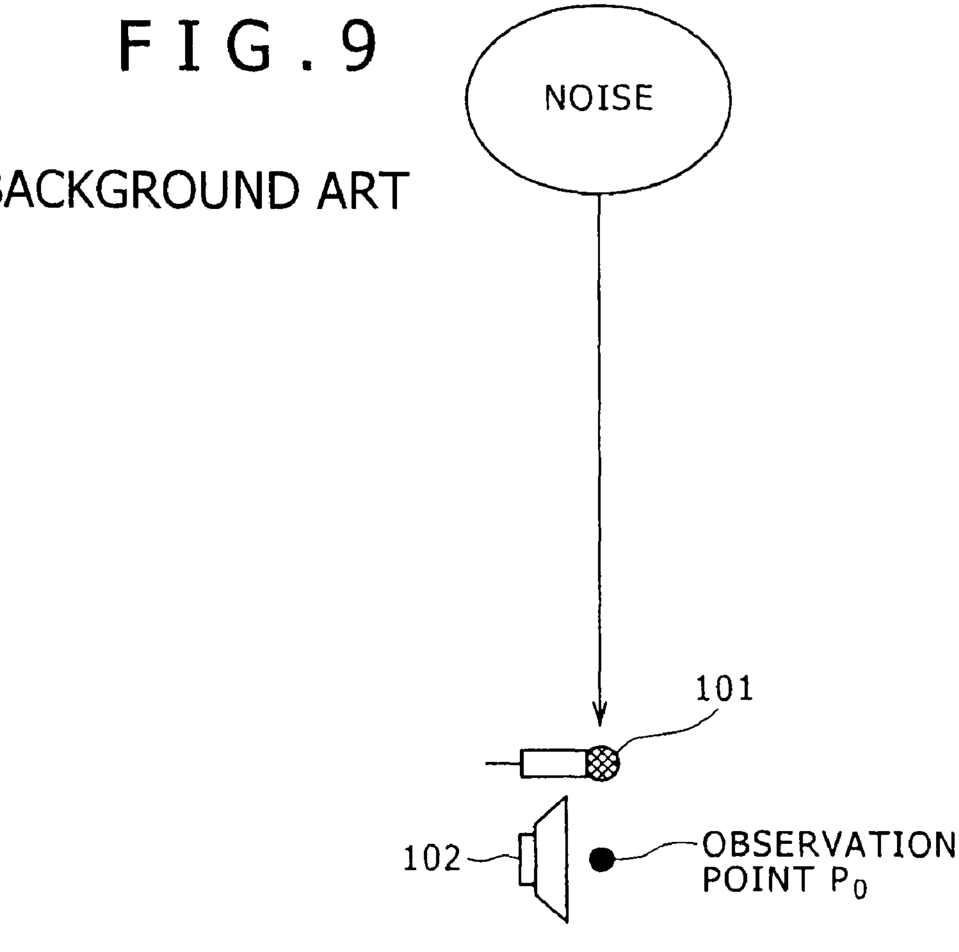
FIG. 9 BACKGROUND ART
FIG. 9 is a schematic diagram for describing noise cancellation in the case where a microphone and a loudspeaker are arranged in the proximity of an observation point.
Figure 10A:
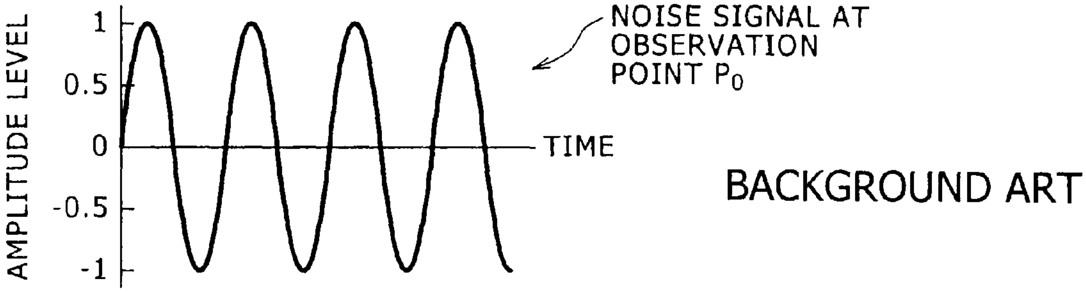
FIGS. 10A, 10B, and 10C are diagrams illustrating waveforms provided in the case where a microphone and a loudspeaker are arranged in the proximity of an observation point.
Figure 10B:
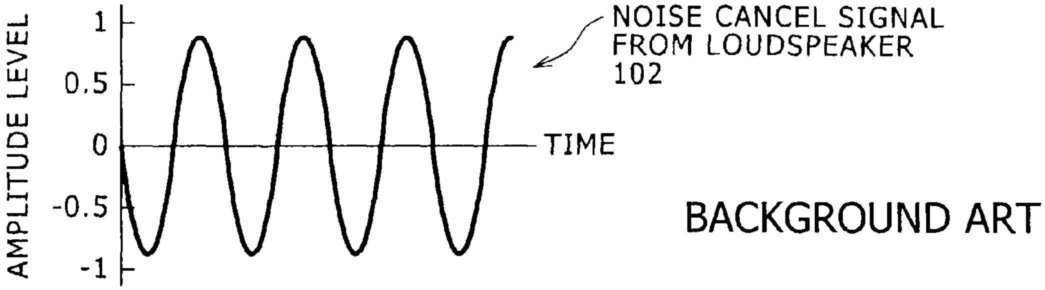
BACKGROUND ART FIG. 10B
Figure 10C:
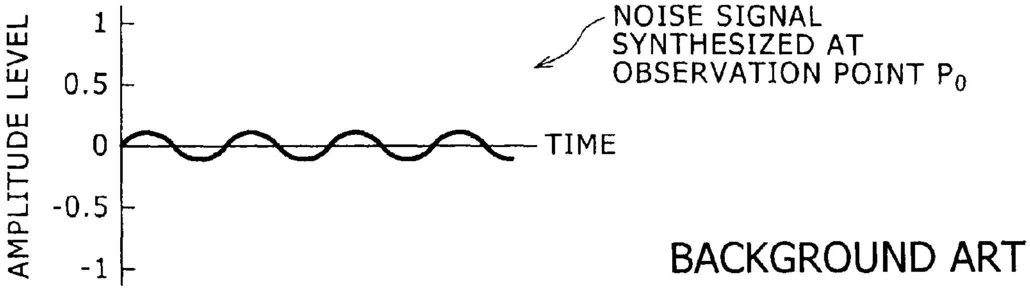
BACKGROUND ART FIG. 10C
Figure 11:
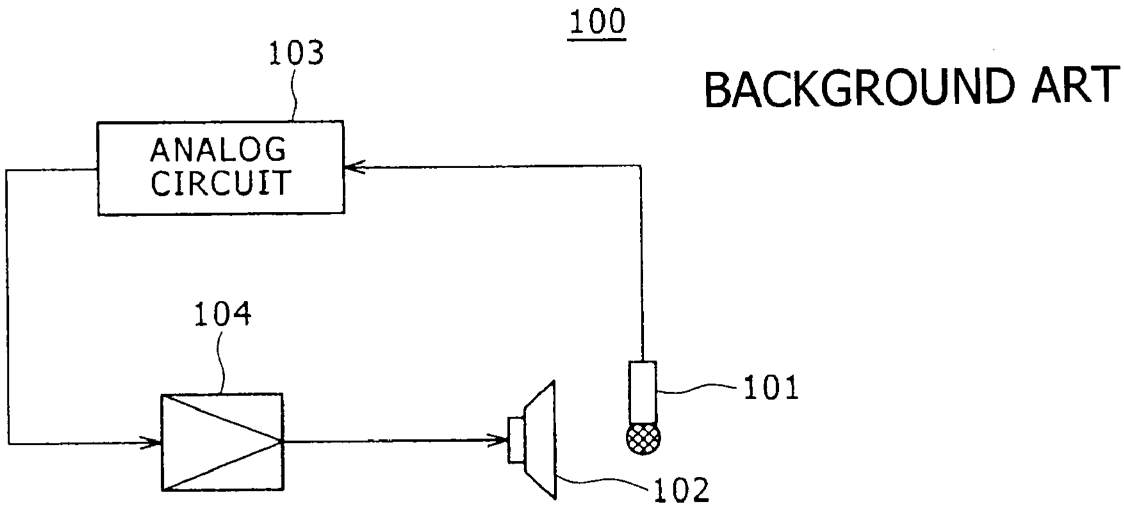
FIG. 11 is a block diagram illustrating an exemplary configuration of a related-art noise canceling apparatus.
Figure 12:
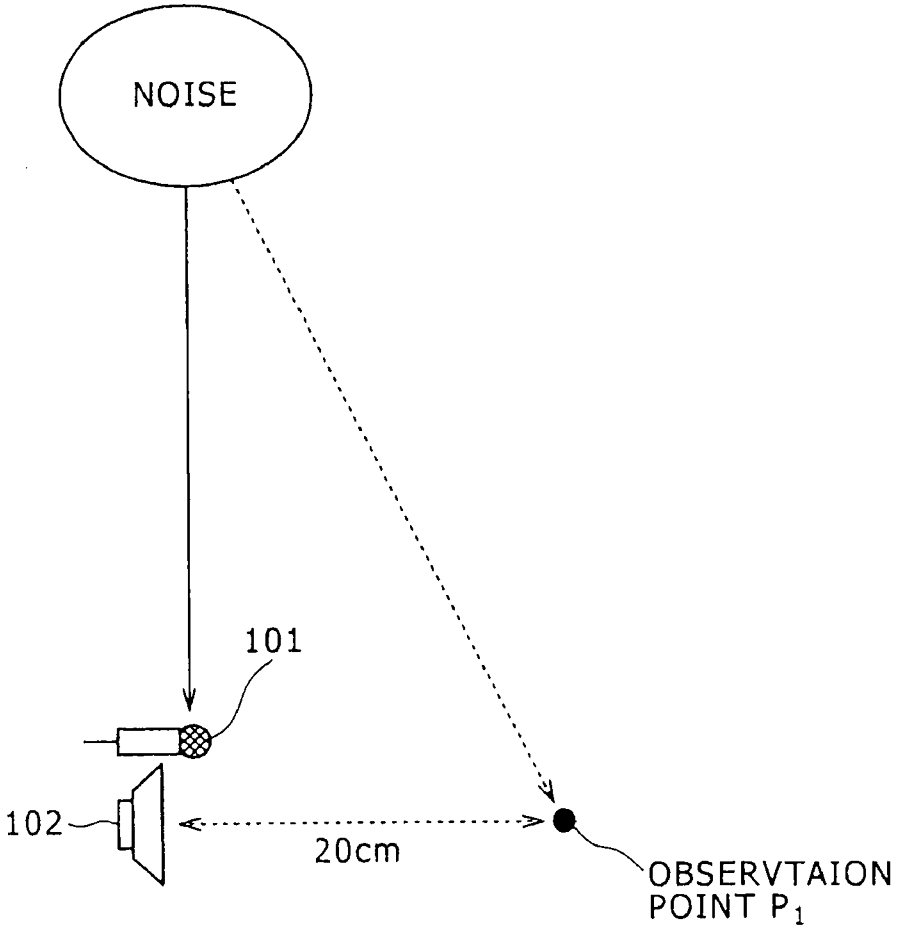
FIG. 12 is a schematic diagram illustrating noise cancellation in the case where a microphone and a loudspeaker are arranged away from an observation point.
Figure 13A:
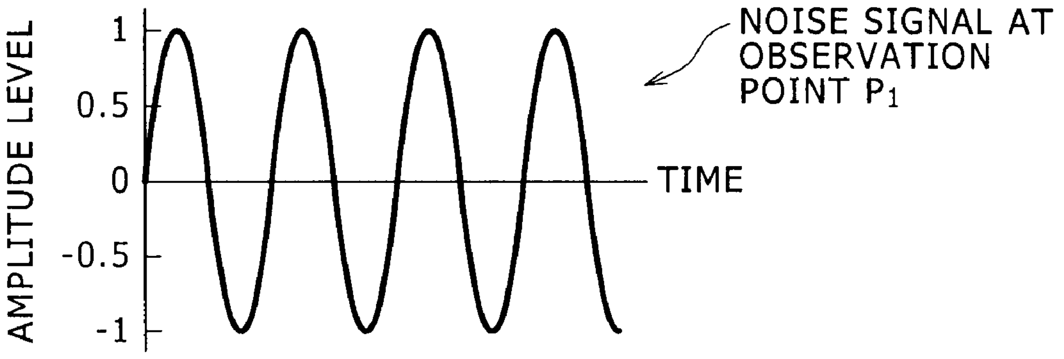
FIGS. 13A, 13B, and 13C are diagrams illustrating waveforms of signals provided in the case where a microphone and a loudspeaker are arranged away from an observation point.
Figure 13B:
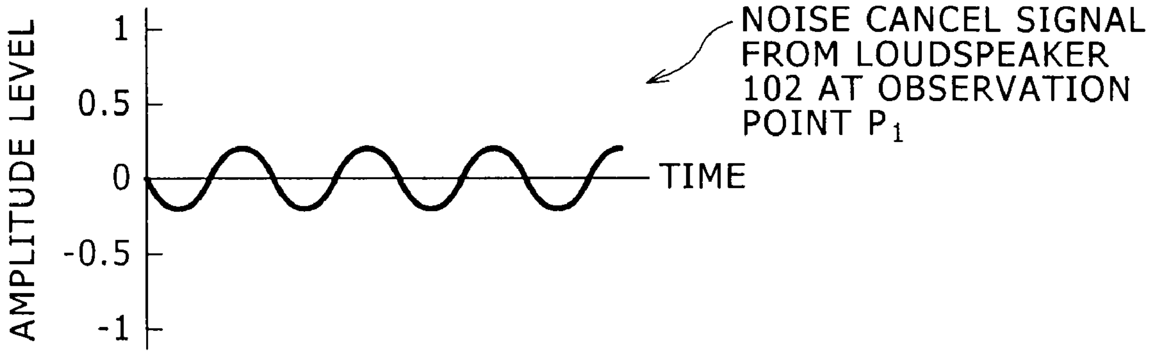
Figure 13C:
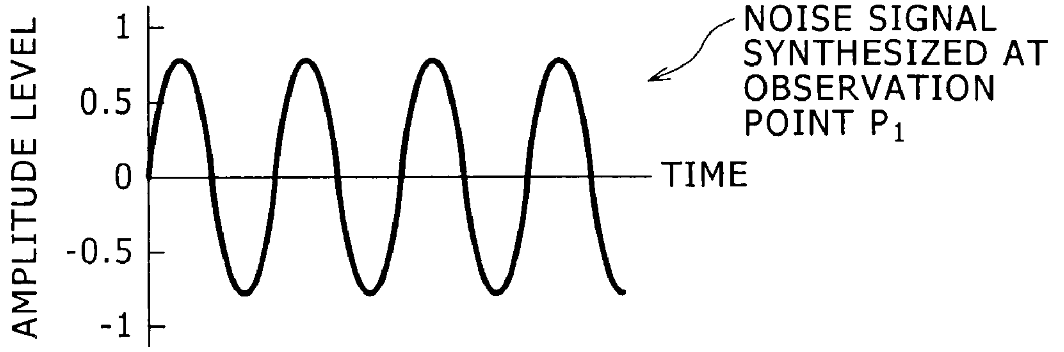

FIG. 8 shows an installation example in which a noise canceling apparatus according to the second variation to the above-mentioned embodiment is applied automobiles. In this second variation, a sensor block 54 is arranged in the proximity of a main loudspeaker 12*a* as shown in FIG. 8 for example.

The sensor block 54, based on an ultrasound sensor or a camera, measures the distance from the microphone 11 and the main loudspeaker 12*a* to observation point P (in this example, the position of user's head). In accordance with a result of the measurement, the amplitude level of a positive-phase signal to be outputted from the sub loudspeaker 12*b* is varied.

For example, if observation point P gets away from the microphone 11 and the main loudspeaker 12*a*, the amplitude level of a positive-phase signal to be outputted from the sub loudspeaker 12*b* is increased. Consequently, the amplitude level of a noise cancel signal to be entered in the microphone 11 is decreased, thereby maximizing the effect of noise cancellation at a spot separated away from the main loudspeaker 12*a*.

On the other hand, if observation point P gets near the microphone 11 and the main loudspeaker 12*a*, the amplitude level of a positive-phase signal to be outputted from the sub loudspeaker 12*b* is decreased. Consequently, the amplitude level of a noise cancel signal to be entered in the microphone 11 is increased, thereby maximizing the effect of noise cancellation at a spot near the main loudspeaker 12*a*.

As described above, in the second variation to the above-mentioned embodiment of the invention, the amplitude level of a positive-phase signal to be outputted from the sub loudspeaker 12*b* is variable in accordance with the distance from the microphone 11 measured by the sensor block 54. This configuration maximizes the effect of noise cancellation at observation point P even if the position of observation point P changes.

It should be noted that the second variation has been described by use of an example in which the sensor block 54 is arranged for the noise canceling apparatus 1 of the above-mentioned embodiment of the invention; however, the variation is not limited to this configuration. For example, this configuration is also applicable to the noise canceling apparatus 1' of the above-mentioned first variation.

While one embodiment of the invention, the first variation thereto and the second variation to that embodiment have been described by using specific terms, such description is for illustrative purpose, and it is to be understood that further changes and variations may be made without departing from the spirit or scope of the following claims.

In the above-mentioned embodiment and the first variation thereto, only a noise cancel signal is outputted from the main loudspeaker 12*a* or the loudspeaker 12; however, the embodiment and the first variation are not limited to this configuration. For example, in the noise canceling apparatus 1 and the noise canceling apparatus 1', an audio signal, such as music, may be superimposed on a noise cancel signal to simultaneously output the noise cancel signal and the audio signal from the loudspeaker 12.

In the above-mentioned examples, the noise canceling apparatuses according to an embodiment of the invention are applied to automobiles; however, the noise canceling apparatuses according to an embodiment of the invention may also applied to other vehicles, such as airplanes and ships. Further, in addition to vehicles, the noise canceling apparatuses according to an embodiment of the invention are applicable to places where individual user seats are arranged, such as in indoor facilities including movie theaters and lecture halls, and to household AV (Audio/Video) systems.

The present application contains subject matter related to that disclosed in Japanese Priority Patent Application JP 2008-118022 filed in the Japan Patent Office on Apr. 30, 2008, the entire content of which is hereby incorporated by reference.

It should be understood by those skilled in the art that various modifications, combinations, sub-combinations and alterations may occur depending on design requirements and other factor in so far as they are within the scope of the appended claims or the equivalents thereof.

What is claimed is:

1. A noise canceling apparatus comprising:

a microphone configured to pick up ambient sound as noise;

a first signal generator configured to receive a signal from said microphone to generate a noise cancel signal that is inverted in phase to said signal received from said microphone and has an amplitude level considered with an attenuation in accordance with a distance from said microphone to an observation point separated away from said microphone;

a first loudspeaker configured to be arranged in the proximity of said microphone and output said noise cancel signal;

a second signal generator configured to receive said signal from said microphone to generate a positive-phase signal that has the same phase as that of said signal from said microphone; and a second loudspeaker configured to be arranged in the proximity of said microphone and output said positive-phase signal;

wherein said noise cancel signal outputted from said first loudspeaker is attenuated by said positive-phase signal outputted from said second loudspeaker to let a noise cancel signal having an amplitude level substantially equal to that of a noise cancel signal observed at said observation point reach said microphone.

2. The noise canceling apparatus according to claim 1, wherein said second signal generating block sets an amplitude level of said positive-phase signal in accordance with a distance from said microphone to said observation point.

3. The noise canceling apparatus according to claim 1, further comprising:

a sensor configured to measure a distance from said microphone to said observation point;

wherein, in accordance with a distance measured by said sensor, an amplitude level of said positive-phase signal generated by said second signal generator is variable.

4. The noise canceling apparatus according to claim 1, wherein said second speaker is arranged such that a distance up to said microphone is nearer than a distance from said first loudspeaker to said microphone, and oriented such that said positive-phase signal to be outputted will not reach said observation point.

5. A noise canceling apparatus comprising:

a microphone configured to pick up ambient sound as noise;

a first signal generator configured to receive a signal from said microphone to generate a noise cancel signal that is inverted in phase to said signal received from said microphone and has an amplitude level considered with an attenuation in accordance with a distance from said microphone to an observation point separated away form said microphone;

a loudspeaker configured to be arranged in the proximity of said microphone and output said noise cancel signal;

a second signal generator configured to receive said noise cancel signal generated by said first signal generator to generate a positive-phase signal inverted in phase to said noise cancel signal; and a synthesizer configured to synthesize said signal from said microphone and said positive-phase signal;

wherein said noise cancel signal outputted from said loudspeaker and picked up by said microphone is attenuated by the synthesis with said positive-phase signal in said synthesizer to provide a noise cancel signal having an amplitude level substantially equal to that of a noise cancel signal observed at said observation point.

6. The noise canceling apparatus according to claim 5, wherein said second signal generator sets an amplitude level of said positive-phase signal in accordance with a distance from said microphone to said observation point.

7. The noise canceling apparatus according to claim 5, further comprising:

a sensor configured to measure a distance from said microphone to said observation point;

wherein, in accordance with a distance measured by said sensor, an amplitude level of said positive-phase signal generated by said second signal generator is variable.

8. A noise canceling method comprising the steps of:

receiving a signal from a microphone picks up ambient sound as noise to generate a noise cancel signal that is inverted in phase to said signal received from said microphone and has an amplitude level considered with an attenuation in accordance with a distance from said microphone to an observation point separated away from said microphone;

outputting said noise cancel signal from a first loudspeaker arranged in the proximity of said microphone and;

receiving said signal from said microphone to generate a positive-phase signal that has the same phase as that of said signal from said microphone; and outputting said positive-phase signal from a second loudspeaker arranged in the proximity of said microphone;

wherein said noise cancel signal outputted from said first loudspeaker is attenuated by said positive-phase signal outputted from said second loudspeaker to let a noise cancel signal having an amplitude level substantially equal to that of a noise cancel signal observed at said observation point reach said microphone.

9. A noise canceling method comprising the steps of:

receiving a signal from a microphone that picks up ambient sound as noise to generate a noise cancel signal that is inverted in phase to said signal received from said microphone and has an amplitude level considered with an attenuation in accordance with a distance from said microphone to an observation point separated away from said microphone;

outputting said noise cancel signal from a loudspeaker arranged in the proximity of said microphone;

receiving said noise cancel signal generated by said first signal generating step to generate a positive-phase signal inverted in phase to said noise cancel signal; and synthesizing said signal from said microphone and said positive-phase signal;

wherein said noise cancel signal outputted from said loudspeaker and picked up by said microphone is attenuated by the synthesis with said positive-phase signal in said synthesizing step to provide a noise cancel signal having an amplitude level substantially equal to that of a noise cancel signal observed at said observation point.

10. The noise canceling apparatus according to claim 1, wherein said first loudspeaker is configured to output said noise cancel signal toward said observation point.

11. The noise canceling apparatus according to claim 1, wherein said noise cancel signal cancels at least a portion of said ambient sound at said observation point.

* * * * *